United States Patent [19]
Levine et al.

[11] Patent Number: 6,129,746
[45] Date of Patent: Oct. 10, 2000

[54] IMPLANTABLE CARDIAC STIMULATION DEVICE WITH DYNAMIC SELF-REGULATION OF THE FREQUENCY OF AUTOMATIC TEST FUNCTIONS AND THE RECORDATION THEREOF

[75] Inventors: Paul A. Levine, Newhall; Lisa P. Weinberg, Moorpark, both of Calif.

[73] Assignee: Pacesetter, Inc., Sylmar, Calif.

[21] Appl. No.: 09/211,314

[22] Filed: Dec. 14, 1998

[51] Int. Cl.⁷ .................................................. A61N 1/37
[52] U.S. Cl. ............................................................ 607/27
[58] Field of Search .................................. 607/5, 27, 28, 607/29, 63; 600/509, 510

[56] References Cited

U.S. PATENT DOCUMENTS

| | | | |
|---|---|---|---|
| 4,708,142 | 11/1987 | DeCote, Jr. | 607/28 |
| 5,209,228 | 5/1993 | Cano et al. | 607/27 |

OTHER PUBLICATIONS

M.L. Dohrmann, M.D. & N.F. Goldschlager, M.D., "Myocardial Stimulation Threshold in Patients with Cardiac Pacemakers: Effect of Physiologic Variables, Pharmacological Agents, Lead Electrodes," pp. 527–537, Cardiology Clinics, vol. 3, No. 4, Nov. 1985.

*Primary Examiner*—William E. Kamm

[57] ABSTRACT

An implantable cardiac device, such as a pacemaker or an implantable cardioverter-defibrillator that has a control unit which is adapted to sample a time-varying parameter relating to either the patient's changing physiological condition or to the delivery of therapeutic electrical stimulation pulse to the heart at a sampling frequency. The control unit is adapted to increase the sampling frequency when the variation between successive measurements of the parameter exceed a preselected value. The control unit is further adapted to decrease the sampling frequency when the variation between successive measurements of the parameter are less than a preselected value. In alternate embodiments, the parameter to be sampled is capture threshold, sensing threshold, lead-tissue impedance, and battery performance.

8 Claims, 5 Drawing Sheets

IMPLANTABLE CARDIAC STIMULATION DEVICE WITH DYNAMIC SELF-REGULATION OF THE FREQUENCY OF AUTOMATIC TEST FUNCTIONS AND THE RECORDATION THEREOF

FIELD OF THE INVENTION

The present invention relates to an implantable cardiac stimulation device and, more particularly, an implantable cardiac stimulation device having the capability of recording device performance (e.g., capture threshold, lead impedance, or other time-varying body function measurements) in a more efficient manner.

BACKGROUND OF THE INVENTION

Implantable cardiac stimulation devices, such as pacemakers and implantable cardioverter-defibrillators, are devices that are implanted within the body of a patient so as to correct and regulate heart function. Typically, these types of devices include one or more leads that are adapted to be implanted within the body of the patient so as to be adjacent the heart in order to deliver therapeutic electrical stimulation pulse to the heart. Further, these devices generally also include a control unit having a processor, that is positioned within a casing that is also adapted to be implanted within the body of the patient. Over time, the control units of implantable cardiac devices have become increasingly sophisticated thereby allowing the control units to tailor the therapeutic electrical stimulation that is provided to the heart to optimize device performance and heart regulation.

For example, current generation pacemakers are capable of detecting intrinsic heart activity so that the pacemaker only provides pacing pulses when the intrinsic heart activity is missing. Moreover, these types of more sophisticated implantable cardiac devices also incorporate numerous sensors which provide data to the control unit enabling the control unit to optimize the therapeutic stimulation provided to the heart.

Implantable cardiac devices also generally include telemetry circuits that allow a treating physician to download instructions to the control unit following implantation. Further, the telemetry circuit can also be used to allow the treating physician to retrieve stored information about heart activity and device performance. The treating physician may periodically want to review device performance or heart activity data to ensure that the device is providing therapy in desired manner. Consequently, current generation implantable cardiac devices incorporate memories and the processors in these devices are adapted to periodically sample and record various performance parameter measurements in the storage means.

One difficulty, however, is that implantable cardiac devices have significant limitations on both space and battery power which affect the ability of the processor to record data for subsequent review. Specifically, the space within the casing containing the control unit is usually at a premium as the overall size of the implanted casing is preferably kept to as small as possible to minimize patient discomfort. The casing must be able to accommodate the processor and the circuitry that produces the therapeutic waveform so that there is not much space that can accommodate memory devices for storing data.

Moreover, the sampling and recording of device or heart performance data also consumes power from the battery which reduces the longevity of the cardiac device. The more power that is consumed in the sampling and recording of device or heart data results in less power being available in the long term to provide needed therapeutic stimulation to the heart, necessitating earlier replacement of the pacemaker.

A still further effect of repetitive sampling and recording of device or heart performance data is the consumption of available random access memory (RAM), which may eventually impact pacemaker function. Space limitation in pacemaker housings gives rise to limitations on sizing of memory areas which, therefore, places design demands for the efficient use of available memory.

As a consequence, implantable cardiac devices are generally set to sample and then record device or heart parameters at periodic intervals. The periodic sampling of device or heart parameters reduces the overall drain on the battery particularly when the parameter is sampled by providing a test pulse to the heart. The periodic recording of the device data reduces the overall size requirements of the memory and further reduces the consumption of battery power during the recording process. However, if the selected parameter is sampled and recorded at a fixed frequency, and the performance of the device or heart changes during the interval between the recording of the parameter, important data relating the change in the parameter may be lost.

For example, one parameter that is periodically sampled and recorded by prior art pacemakers is capture threshold. Specifically, the pacemaker may be adapted to periodically provide a series of pacing pulses of decreasing magnitude to determine at what magnitude the delivered pacing pulse fails to induce a paced beat response. The last magnitude value that resulted in a paced beat response is known as the capture threshold. The capture threshold parameter can be used to set the magnitude of the pacing pulse to be delivered to the heart at some safety margin above the capture threshold to ensure the delivered pacing pulse induces a paced beat response of the heart. In autocapture pacing devices, the output is typically set to a value which is much closer to the threshold value, since more frequent capture threshold measurements are continuously being made to ensure that the output will be adequate to obtain capture even as changes in the capture threshold varies, which may be indicative of a developing problem with the lead or alterations in the clinical status of the patient. The capture thresholds are often recorded in the memory for subsequent review and analysis by the treating physician to detect these changes in threshold value which, as noted above, may be indicative of lead and implantation conditions.

In some devices, the capture threshold device parameter is measured on a relatively frequent basis for autocapture type devices, e.g., once or twice a day, and the resulting measurement is recorded in memory on a somewhat less frequent periodic basis, e.g., once or twice a week. However, it is understood that the capture threshold device parameter changes over time.

For example, immediately following implantation, the capture threshold is usually relatively low as the lead is positioned immediately adjacent the inner wall of the heart. However, inflammation of the heart tissue surrounding the implanted lead then begins to increase the impedance at the implantation site which results in the capture threshold increasing in magnitude. Subsequently, a fibrous tissue forms around the implanted lead adjacent the inner wall of the heart which results in an increase in the effective area of the electrode that is delivering the pacing pulse to the heart. This membrane results in a decrease in the capture threshold such that the capture threshold essentially stabilizes at a particular value.

The growth of the fibrous tissue and the resulting change in the capture threshold generally occurs over a one- to two-month period and is typically referred to as the period of lead maturation. Similarly, the lower, relatively stable, value of the capture threshold following the acute phase will typically persist, in the absence of any lead implantation problem, for an extended period of time. This period of relatively stable capture threshold is typically referred to as the chronic phase of lead implantation.

It is desirable to have a relatively considerable amount of data during the lead maturation so that the treating physician can monitor whether the change in the capture threshold indicates that the leads have been properly implanted. However, once the acute phase has ended, the need to sample and record the capture threshold data with heightened frequency is reduced and such heightened frequency recording can result in a significant drain on the battery and can also result in the memory being filled by less valuable data. Further, it is possible that more valuable data may even be overwritten by less valuable data. It is also desirable to allow available RAM to be more efficiently used to report periods of stability but to also report periods of instability in far greater detail than would be accomplished with a fixed preset sampling rate.

In many prior art devices, the treating physician can adjust the sampling and recording frequency of the device parameter using the telemetry circuit.

However, the patient may not return to the treating physician at an appropriate time for the adjustment of the sampling and recording frequency. Moreover, there may be a sudden change in the implanted device which may result in a significant change in the device or heart parameter. For example, if a lead becomes broken or partially dislodged, the capture threshold may vary significantly from the typical chronic phase value.

Other conditions may arise that would not result in a subsequent operative intervention, but would be managed totally by automatic or manual programming of the system. These would include, for example, capture threshold changes due to lead-tissue interface problems as may occur with progression of a patient's intrinsic disease process, concomitant diseases, such as kidney failure, which will cause the serum potassium level to rise, which will cause the capture threshold to rise, or the administration of a medication, which may be newly known to affect capture. Accordingly, if the treating physician has set the implanted cardiac device to record the device parameter at a lower frequency, critical data relating to the change in the device or heart parameter may not be captured.

Hence, there is a need for an implantable cardiac device that is capable of recording device or heart parameter data where the sampling and recording frequency can be varied by the device depending upon the relative change in the measured parameter. To this end, there is a need for an implanted cardiac device, such as a pacemaker, that is capable of measuring a parameter, such as capture threshold, and sampling and recording this particular parameter at a higher frequency when the parameter measurements are more volatile.

SUMMARY OF THE INVENTION

The aforementioned needs are satisfied by the implantable cardiac device of the present invention, which includes a processor that is adapted to periodically receive signals (sampled at a selected frequency) indicative of a device or heart parameter, determine if the parameter has changed so as to warrant a change in the sampling frequency, and then change the sampling frequency if the measured parameter has changed so as to warrant a corresponding change in the sampling frequency. Moreover, the processor can be further adapted to record the parameter in memory and, in one aspect, record the parameter in memory based upon the change in the device parameter. In this way, the implantable cardiac device can adjust the frequency of sampling the parameter and of recording the resulting measurement in memory so that the sampling and recording occurs more frequently during periods of change in the parameter and less frequently during periods of time when the parameter measurements remain relatively constant.

In one embodiment, the parameter is measured at an initial sampling rate unless the change between sequential parameters indicates that the parameter value is changing. The processor can then increase the sampling rate. In one embodiment, the parameter is stored in the memory at a rate that corresponds to the sampling rate. Hence, the data stored in the memory contains data that is more representative of periods of change in the parameter.

Furthermore, the reason for selectively sampling rates is to provide monitoring as long as is deemed required and clinically meaningful, based upon expected results. A sampling rate of every event would provide a physician with a large degree of precision, without being compromised by memory capacity when the patient is examined not greater than at consecutive six-month intervals; whereas, sampling at a 26-second rate would permit the system to accumulate data for approximately thirteen years with the attendant loss in precision.

In another aspect of the invention, the invention comprises a processor that is adapted to periodically receive signals indicative of a device or heart parameter and the processor is further adapted to record the measured parameter in a memory at a first frequency during a first time period and subsequently record the device parameter in memory the device parameter at a second frequency during a second time period wherein the second frequency is less than the first frequency. The processor can be further adapted to increase the recording of the parameter during the second period to a frequency higher than the second frequency upon the measured device parameter varying more than a preselected amount from previously recorded parameters values.

In another aspect of the present invention, the implantable cardiac device is comprised of a pacemaker that includes a processor which institutes a capture verification function to periodically verify that the pacing pulse will satisfactorily induce heart activity. The processor is further adapted to initiate a capture threshold test and record the measured capture threshold at a first frequency during the acute phase of implantation of the pacing leads. The processor is further adapted to initiate the capture threshold test and record the measured capture threshold values at a second frequency, less than the first frequency, during the chronic phase of implantation. The processor can be further adapted to increase the initiation of the capture threshold test and the recording of the capture threshold when the capture threshold varies by a preselected amount from previous recorded capture thresholds.

Accordingly, a feature of the invention is the automatic adjustment of the frequency with which selected tests are made, based upon the results of such tests. Thus, for example, if a certain test, such as capture threshold testing, is scheduled to be performed every eight hours, the testing schedule will remain fixed until the "system" becomes unstable (wide variation in test results). Once the system becomes unstable, the frequency of performing the test will be automatically increased so as to "re-stabilize" the system.

The foregoing automatic assessment of capture verification may be directed as well to the assessment of selected other time-varying parameters (for example, sensing thresholds, lead impedance, battery voltage and/or impedance, etc.).

The implantable cardiac device of the present invention therefore allows for more efficient testing and recording of device or heart parameters, such as capture threshold, as the frequency of sampling or recording of the parameters corresponds to the change in the measured parameter. Consequently, more data can be recorded in the memory that is indicative of significant events of the implanted cardiac device causing changes in the parameter. This optimizes the use of the memory and can require less use of battery power to sample and record the data during relatively quiescent periods. These and other objects and advantages of the present invention will become more fully apparent from the following description taken in conjunction with the accompanying drawings.

DETAILED DESCRIPTION OF THE INVENTION

Figure 1:
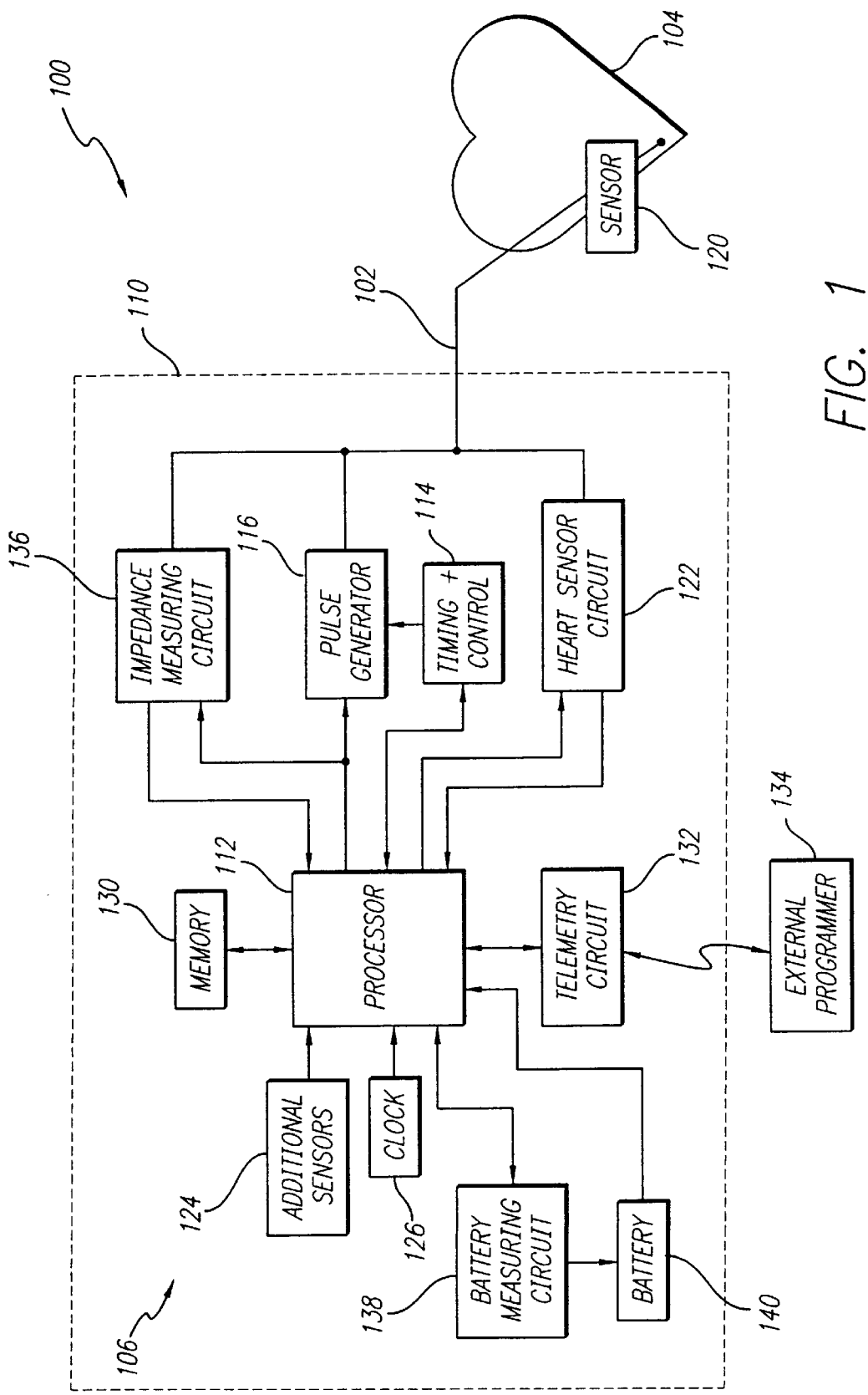
FIG. 1 is a block diagram of an exemplary implantable cardiac device of the preferred embodiment.

Reference will now be made to the drawings wherein like numerals refer to like parts throughout. FIG. 1 is a block diagram illustrating an exemplary implantable cardiac device 100. The cardiac device 100 includes one or more leads 102 that are adapted to be implanted within the body adjacent the heart 104. For example, the leads 102 can be comprised of pacing leads that are adapted to be positioned within the heart 104 so as to be able to deliver a pacing pulse to, for example, the apex of the ventricle of the heart 104 in a well known manner.

The implantable cardiac device 100 also includes a control unit, generally designated 106, that is positioned within a casing 110 that is adapted to be implanted within the body of the patient. The control unit 106 includes a processor 112 that provides output signals to a timing and control circuit 114 so as to induce a pulse generator 116 to generate a therapeutic electrical stimulation pulse or pacing pulses to be delivered to the heart 104 via the leads 102. In one embodiment, the processor 112 provides output signals for the timing and control circuit 114 so as to induce the pulse generator 116 to provide pacing pulses to the heart 104 via the lead 102. In another embodiment, the processor 112 provides output signals to the timing and control circuit 114 so as to induce the pulse generator 116 to produce a defibrillation or cardioversion pulse to be delivered to the heart 104 via the lead 102 in a well known manner.

In this embodiment, the processor 112 also receives a heart signal from a sensor 120 that is positioned adjacent the heart 104 via a heart sensor circuit 122. In one embodiment, the sensor 120 is comprised of a portion of the lead 102 that senses the activity of the heart and provides a signal to the heart sensor circuit 122 which can then provide the processor 112 with an indication of the activity of the heart. In one embodiment, the heart signal is comprised of an intracardiac electrogram (ICEG) signal. The processor 112 can therefore be adapted to deliver the therapeutic electrical stimulation in the form of stimulation pulses via the leads 102 in response to the heart signal provided by the sensor 120 and the heart sensor circuit 122.

Moreover, the implantable cardiac device 100 may also include additional sensors 124, such as activity sensors, minute ventilation sensors, and the like, which provide the processor 112 with additional information. The processor 112 also receives a clock input from a clock 126 that comprises a portion of the control unit 106 so that the processor 112 can time various functions in a well known manner. The processor 112 is also adapted to periodically record data in a memory 130 in a well known manner so that the data can be subsequently downloaded by the processor 112 via a telemetry circuit 132 to an external programmer 134. This recording of data allows a treating physician to review the performance of the implanted cardiac device 100 and the function of the heart 104 during follow-up visits.

The implantable cardiac device may also include an impedance measuring circuit 136 adapted to measure lead-tissue impedance in a conventional way (e.g., by measuring the voltage and current of a stimulation pulse and computing a value for the impedance, or as in constant voltage systems, by measuring the current and using an estimate of the constant voltage to compute the impedance). Lead impedance is another time-varying parameter which changes dramatically during the acute phase and is relatively stable during the chronic phase. Lead impedance may also change abruptly due to a fracture or break in the lead. Advantageously, the present invention adapts the frequency of the lead impedance measurements anytime there is a significant change detected by the processor 112.

The present invention may also include a battery measuring circuit 138 for measuring the capacity of the device's battery 140. In accordance with the present invention, the battery measurement circuit 138 will be triggered to take more frequent measurements as the battery parameter being monitored (e.g., voltage, impedance, capacity, etc.) begins to reach its recommended replacement time. The battery measurement circuit 138 will be triggered less frequently at its beginning-of-life (BOL), and therefore, current drain and memory are thereby conserved.

It will be appreciated that the implantable cardiac device 100 is similar to implantable cardiac devices of the prior art and can encompass the functionality of a pacemaker or an implantable cardioverter-defibrillator (ICD) or both. As will be described in greater detail below, the implantable cardiac device 100 is adapted to be able to measure particular device or heart parameters and record these parameters in the memory 130 in a more efficient manner. It will be appreciated from the following discussion that the manner in which the implantable cardiac device 100 samples and records the data in the memory 130 can be used in any of a number of different implantable cardiac devices without departing from the spirit of the present invention.

More specifically, the control unit 106 of the implantable cardiac device 100 is adapted to periodically measure both device performance parameters and heart function parameters to ensure that the device 100 is operating appropriately and is providing appropriate therapy to the heart 104. These parameters can include such things as sensitivity thresholds for the various sensors to ensure that the sensors are appropriately detecting various heart activities, capture thresholds to ensure that the therapeutic waveforms being delivered to the heart are resulting in the desired heart activity, and various other parameters. The exact device or heart parameter that is periodically tested will, of course, vary depending upon the configuration of the implantable cardiac device. However, the implantable cardiac device 100 is adapted to periodically sample and record the parameter in the memory 130 for subsequent review by the treating physician via the external programmer 134 and the telemetry circuit 132.

Figure 2:
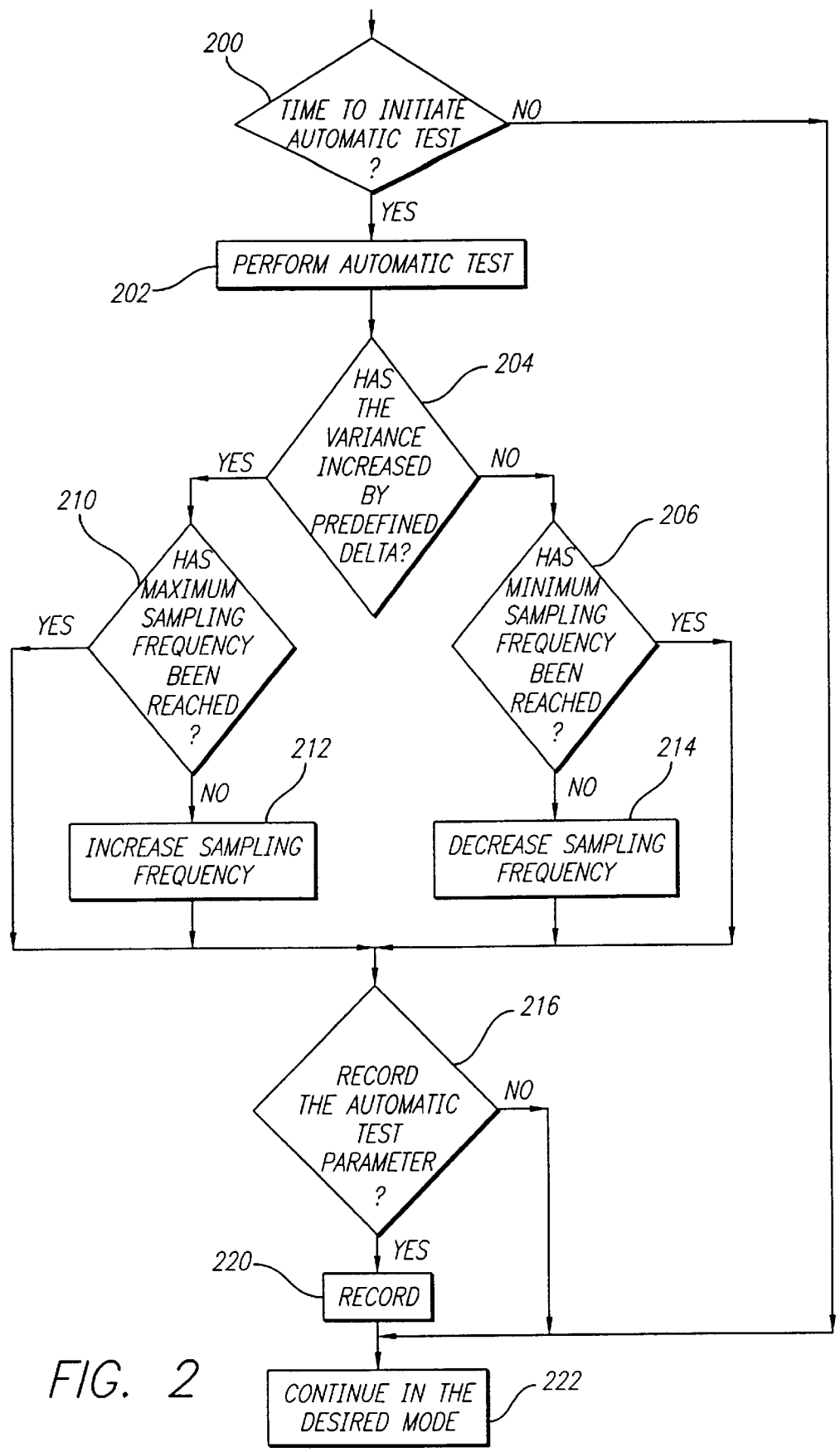
FIG. 2 is an exemplary flowchart illustrating the operation of the implantable cardiac device of FIG. 1 as it implements a sample and record parameter function.

FIG. 2 is a flowchart which illustrates the operation of the processor 112 as is periodically measures a given parameter, and then records the parameter measurements in the memory 130. The flowchart of FIG. 2 is a top level flowchart which illustrates the operation of the processor 112 as it records any of a number of different parameters.

However, as will be described in greater detail below, particular parameters such as capture threshold can be sampled and stored in memory at a frequency that is dependent upon the rate of change in the measured parameter. In particular, the processor 112 is adapted to increase the sampling rate and also increase the frequency of recording the sampled data in the memory 130 when the measured parameter data appears to have changed significantly as compared to a previously obtained measurement, a desire value or some other measurement point. In this way, increased data can be obtained during periods of change of the parameter, however, during periods of time when the parameter is relatively stable, the consumption of limited battery power to measure the parameter and the consumption of limited available memory space to store the relatively stable data can be reduced.

Specifically referring to FIG. 2, the processor 112 initially determines, in a decision state 200, whether it is time to initiate the automatic test. The processor 112 is ascertaining whether the time period for obtaining the parameter measurement has occurred. As discussed above, the control unit 106 typically includes a clock 126 that provides a clock input to the processor 112. This clock input can be used by the processor 112 to determine whether the time period for initiating a parameter sampling function has occurred. It will be appreciated that upon implantation, a default time period will likely be set by the implanting physician. However, as will be discussed in greater detail below, in this embodiment the period for sampling the parameter will increase or decrease depending upon the change in value of the measured parameter.

If the processor 112 determines, in decision state 200, that the time to initiate the automatic test of the parameter has occurred, the processor 112 then performs the automatic test in state 202. The manner in which the automatic test is performed to sample the parameter, of course, varies depending upon the parameter that is to be sampled. For example, if the parameter to be sampled is the capture threshold, the processor 112 will perform a function whereby a series of pacing pulses of decreasing magnitude will be provided to the heart until the pacing pulses fail to result in a paced beat of the heart. This process will be described in greater detail in reference to FIG. 5 herein below. Alternatively, if another parameter, such as sensing threshold is to be measured or sampled, the processor 112 would then perform a function whereby this particular parameter would be measured.

After performing the automatic test, the processor 112 then determines, in decision state 204, whether the sampled parameter has varied by a predefined delta from a preselected value of the parameter. The predefined delta can be the change between two successive measurements of the parameter or it can also be the variation of the measured parameter from a preselected value. As will be explained in greater detail below, the processor 112 in this embodiment is adapted to adjust the sampling rate of the parameter when the parameter is changing. In this way, the processor 112 can sample and record more measurements during periods of change of the parameter, thereby providing more information to the treating physician about the interval of time when the parameter is changing, but can also conserve energy and memory space by not sampling or storing the parameter as frequently during time intervals when the parameter remains relatively steady.

In the event that the processor 112 determines in decision state 204 that the variation of the measured parameter value exceeds the predefined delta, the processor 112 is then adapted to increase the sampling frequency of the parameter provided that the sampling frequency already does not exceed a preselected maximum sampling frequency. Consequently, the processor 112 then determines, in decision state 210, whether the current sampling frequency is equal to the maximum sampling frequency for this particular parameter. If the maximum sampling frequency has not been reached, the processor 112 then proceeds to increase the sampling frequency value in state 212 by a predefined increment.

The sampling frequency can be increased by a predefined increment that may be preferably set by a treating physician. In this way, the frequency with which the parameter will be subsequently measured is increased in response to a change in the parameter from either the previously measured parameter value or from a preselected optimum parameter value.

Alternatively, if a processor 112 determines in decision state 204 that the variation between the parameter obtained in state 202 from the previously recorded value or the optimal value is less than the predefined delta, then the processor 112 does not need to sample the parameter as frequently as the parameter is not changing significantly. Consequently, the processor 112 then determines, in decision state 206, whether the sampling frequency for the parameter is at a preselected minimum sampling frequency. If the sampling frequency is not at the preselected minimum value, the processor 112 then decreases the sampling frequency by a predefined increment in state 214. In this way, the processor 112 can decrease the frequency with which the parameter is sampled when the parameter is remaining relatively constant. Consequently, the processor 112 can reduce the drain on the battery to obtain the sample, as well as reducing RAM usage.

Once the processor 112 has adjusted the sampling frequency in either state 212 or 214, the processor 112 then determines, in decision state 216, whether to record the measured parameter value in the memory 130. In one embodiment, the processor 112 may be adapted to record the measured parameter value measured in state 202 after each sampling cycle. Alternatively, the processor 112 may be further adapted to only record the parameter value measured in state 202 based upon whether the measured parameter value varied by a selected amount, such as the predefined delta, as determined in decision state 204, from either the previously measured parameter value or the target parameter value. In this way, the processor 112 can optimize usage of the limited available space in the memory 130 so that the stored data is more representative of periods of change in the measured parameter.

If the processor 112 determines in decision state 216 that the parameter value measured in state 202 is to be recorded, the processor 112 then proceeds to record the value in state 220 along with a time indication as to when the value was recorded in the memory 130. Subsequently, the processor 112 then returns, in state 222, to delivering therapeutic stimulation to the heart in the desired mode.

It will be apparent from the foregoing that the processor 112 is capable of periodically sampling a parameter and recording the measured value in a memory for subsequent review by a treating physician. The processor 112 is further adapted to adjust the frequency with which the parameter is tested, or sampled, and also independently adjust the frequency with which the measured parameter value is recorded in the memory based upon the variation between the measured parameter value and a previously recorded value or some preselected value. In this way, the processor 112 can more efficiently test and record a particular parameter for review by a treating physician. As can be seen in FIG. 2, by placing the Perform Automatic Test (Block 202) within the loop (Blocks 200–222), the Automatic Test is performed more or less frequently, as determined by the patient's physiological needs, thereby conserving current drain by omitting unnecessary testing. Accordingly, both the frequency of the automatic test and the recordation of the measured parameters are self-regulated by the implantable stimulation device.

The exact process by which a particular heart or device parameter is measured is, of course, dependent upon the parameter that is to be measured. As discussed above, these parameters can include such things as sensing thresholds, capture thresholds and the like. In one particular embodiment of the present invention, the implantable cardiac device 100 is adapted to provide pacing stimulus to the heart 104 via the leads 102. The implantable cardiac device 100 is further adapted to periodically ascertain the magnitude and duration of the pacing pulse that will result in capture of the heart, i.e., result in the heart emitting a paced beat in response to the pacing pulse. Being able to subsequently review the capture threshold parameter provides a treating physician with an effective diagnostic tool for assessing device performance and the condition of the patient.

Figure 3:
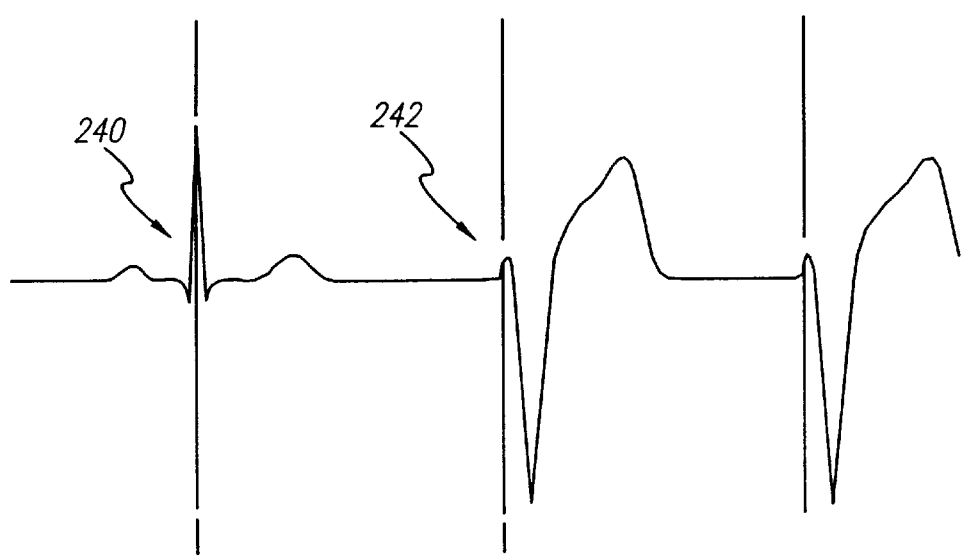
FIG. 3 is a cardiac waveform illustrating the sensor input received by the implantable cardiac device of FIG. 1 after a pacing pulse has been delivered.
Figure 4:
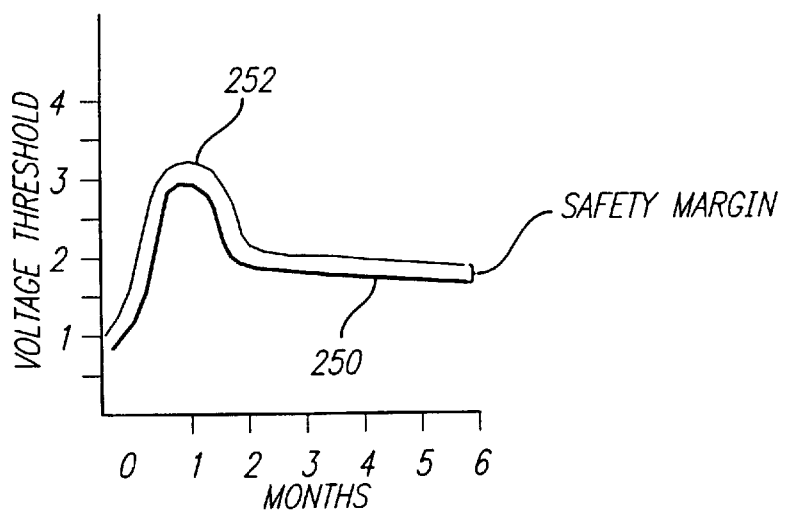
FIG. 4 is a diagram illustrating the expected capture threshold data of a pacing lead of the implantable cardiac device of FIG. 1 over a period of time.

Determining the capture threshold of the heart typically involves providing a series of decreasing magnitude pacing pulses to the heart until the pulses no longer result in a paced beat of the heart. This process can result in a significant consumption of limited battery power. However, this embodiment of the implantable cardiac device 100 is adapted to adjust the frequency with which the capture threshold is sampled based upon the variation of capture threshold measurement from previously measured capture threshold values so that the capture threshold will be sampled at a lower frequency when the capture threshold is relatively stable which results in less consumption of limited battery power. The process by which the capture threshold is measured will now be described in conjunction with FIGS. 3 through 5. FIGS. 3 and 4 are provided for background to facilitate an understanding of capture threshold in pacing applications. In particular, FIG. 3 is a schematic illustration of an electrogram illustrating the difference in waveform shape between an intrinsic cardiac event 240 and a paced beat cardiac event 242 occurring in response to a pacing pulse being delivered to the heart 104 via the leads 102. The significant difference in the illustrated waveforms is detectable by the processor 112 in a well-known manner from the signals being provided to the processor 112 from the sensor 120 via the heart sensor circuit 122. Hence, the processor 112 is capable of providing a pacing pulse to the heart 104 during an appropriate interval via the timing and control circuitry 114 and the pulse generator 116 and then evaluating the resulting waveform to determine whether a paced beat of the heart 104 is induced.

To ascertain the capture threshold, a plurality of pacing pulses are provided to the heart 104 and the magnitude and/or duration of the applied pacing pulses is decreased over time until a paced beat response, such as the response illustrated in the wave form 242, does not occur in response to the delivery of the pacing pulse. The last pacing pulse of the plurality of pulses that induced a paced beat can then be defined as the capture threshold. In this way, a measurement of the capture threshold can be obtained.

FIG. 4 is a schematic illustration which illustrates the typical change in the magnitude of the capture threshold 250 over time following the implantation of the implantable cardiac device. The capture threshold value is largely dependent upon current density across the heart muscle. As illustrated in FIG. 4, the capture threshold 250 of the implanted device 100 starts initially at a low value and then increases to a peak value over the first month or so. This is typically the result of inflammation of the tissue surrounding the electrode which separates the electrode from the excitable myocardium following implantation of the pacing lead. As the inflammation reaction subsides, a thin capsule of fibrous tissue forms around the pacing lead. The fibrous tissue effectively increases the overall surface area of the electrode thereby decreasing the capture threshold. Following the growth of the fibrous tissue, the threshold then typically stabilizes at a relatively fixed value unless some difficulty, such as a lead damage or dislodgment, occurs that affects the capture threshold value. The initial period of time during which the capture threshold is varying significantly, is generally referred to as the acute phase of implantation and the period of time where the capture threshold stabilizes is typically known as the chronic phase of implantation.

With current generation automatic capture pacing system devices, the magnitude of the therapeutic pacing pulses that are to be provided to the heart to regulate heart function is set to always be some safety margin greater than the actual threshold curve 250. The processor 112 is adapted to periodically perform the capture threshold search described above. If the pacing threshold is periodically ascertained, e.g., typically approximately once every twelve hours, the safety margin can be comparatively small as the risk of the pacing pulse failing to result in capture is lower when the actual pacing threshold is known. Desirably, decreasing the safety margin results in a decrease in the amount of power that is consumed with each pacing pulse that is delivered which can thereby prolong the life of the implanted cardiac device.

Figures 1, 5:
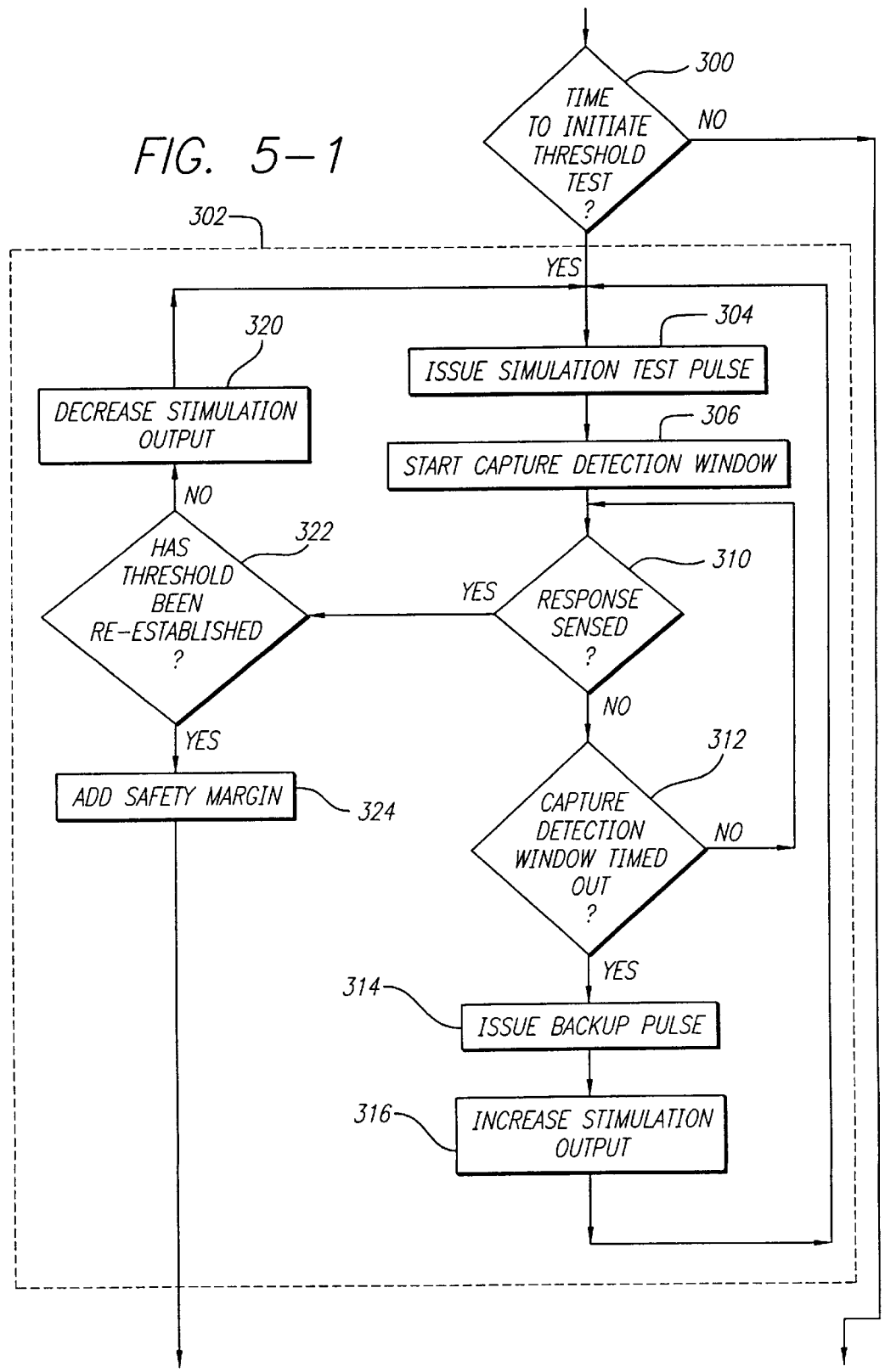
FIG. 5 is an exemplary flowchart illustrating the operation of the implantable cardiac device of FIG. 1 as it periodically samples and records the pacing capture threshold.
Figures 2, 5:
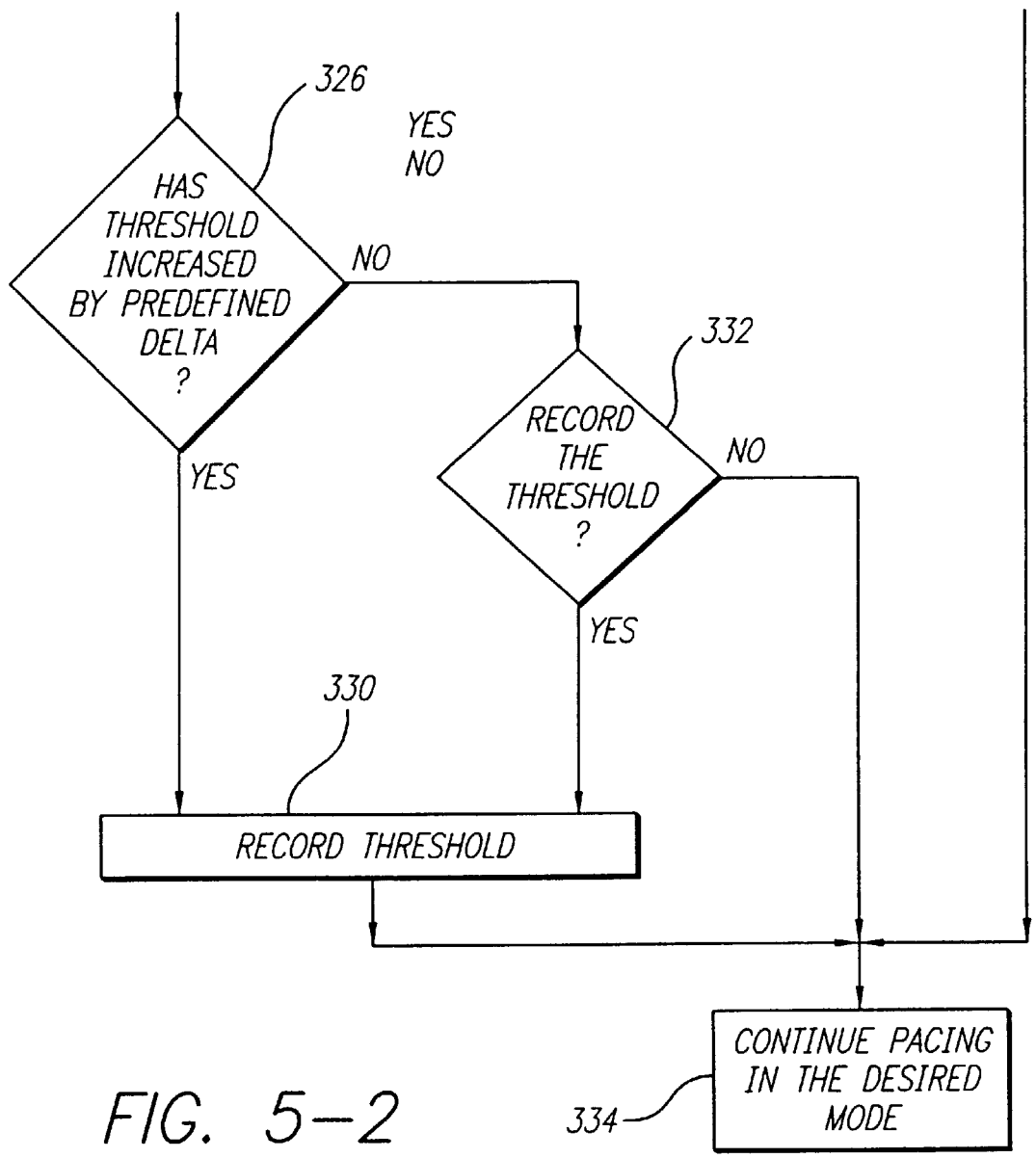

FIG. 5 is an alternate flowchart which illustrates the operation of the processor 112 as the processor 112 measures or samples the capture threshold parameter of an implantable cardiac device configured as a pacemaker. Specifically, the processor 112 initially determines in decision state 300 whether the time to initiate the capture threshold test has occurred. In one embodiment, the capture threshold test is initially performed by the processor 112 at a fixed frequency e.g. approximately once every 12 hours and the device self-regulates the frequency of recording the capture threshold value. However, as was described in conjunction with FIG. 2, if the capture threshold measurements are changing, it may be desirable to increase the frequency with which the capture threshold test is performed. Accordingly, it is within the scope of the invention to modify the embodiment of FIG. 5 to include the ability to self-regulate the frequency of the automatic test, as shown in FIG. 2.

In the fixed-sampling frequency embodiment of FIG. 5, if the processor 112 determines in decision state 300 that the time for sampling the capture threshold has occurred, the processor 112 then performs a threshold search function 302 that is comprised of the states 304 through 324. The threshold search 302 is a process whereby the capture threshold is determined by providing pacing pulses of decreasing magnitude and/or duration to the heart and observing the heart activity until the processor 112 senses a threshold value of the applied pacing pulse at which the heart 104 will not be stimulated by the application of the pacing pulse.

Specifically, in this embodiment, the processor 112 initially issues a stimulation test pulse in state 304 to the heart 104 via the leads 102. This stimulation test pulse is usually provided at a interval which is selected so as to induce a paced event in the heart. Generally, the rate at which the test pulse is provided must be faster than the patient's intrinsic sinus rate so as to result in a paced response by the heart 104. Once the stimulation test pulse has been provided, the processor 112 then starts a capture detection window in state 306. Essentially, the processor 112 is evaluating the signal being received from the sensor 120 via the sensor circuit 122 to look for a paced event waveform such as the waveform 242 (FIG. 3). If no paced response is sensed, the processor 112 then determines in decision state 312 whether the capture detection window has timed out. Basically, there is a preselected period of time following the application of the stimulation test pulse to sense a paced beat response by the heart. If the capture detection window has timed out, the processor 112 then induces, in state 314, the timing and control circuit 114 and pulse generator 116 to provide a back up pulse in state 314. The back up pulse is adapted to ensure that the heart 104 is stimulated into a paced beat. Subsequently, the magnitude and/or duration of the paced output pulse is increased in state 316 and the processor 112 returns to state 304 where a subsequent stimulation test pulse is provided.

However, if the processor 112 determines in decision state 310 that a response to the stimulation test pulse 304 has occurred, the processor 112 then determines in decision state 322 whether the capture threshold value has been reestablished. Essentially, the processor 112 is determining whether the test pulse provided in state 304 has resulted in capture of the heart following the delivery of a test pulse which failed to achieve capture. The processor 112 in this embodiment is adapted to provide a series of decreasing magnitude test pulses, e.g., decreasing in 0.2 volt increments, until the response is lost, subsequently, the magnitude of the test pulse is increased by a preselected increment in state 316 until the processor 112 determines in state 322 that the threshold has been reestablished.

If the processor 112 determines, in decision state 310, that a response was sensed but that the sensed response is not the result of a reestablished threshold, a processor 112 then decreased the stimulation output by the preselected increment in state 320 and provides a stimulation test pulse with the decreased stimulation output in state 304. Alternatively, if the threshold has been reestablished, the processor 112 then adds the safety margin in state 324 to the magnitude of the stimulation test pulse which resulted in the threshold being reestablished and this, value is then used by the processor 112 as the magnitude value of the pacing pulse that will be delivered to the heart upon the processor 112 detecting that the heart is in need of a paced event.

Hence, the threshold search function 302 is capable of ascertaining the capture threshold of the heart 104, i.e., the magnitude and duration of the pacing pulse that will result in the heart providing a paced beat response to the applied pacing pulse. It will, of course, be appreciated that any of a number of different techniques for determining the capture threshold of the heart 104 can be used without departing from the spirit of the present invention.

The processor 112 then determines in decision state 326 whether the measured capture threshold value has increased by a predefined delta. As discussed above, the predefined delta can be the variation between two successive threshold measurements or the difference between the threshold measurement obtained in the threshold search 302 and some preselected target value.

If the threshold parameter has increased by the predefined delta, the processor 112 then proceeds to record data indicative of the capture threshold value in state 330 in the memory 130 along with an indication as to the time that the capture threshold value increased. In this fashion, a significant change in the capture threshold value results in the processor 112 recording the threshold change.

Alternatively, if the processor 112 determines in decision state 326 that the threshold value has not increased by the predefined delta, the processor 112 then determines in decision state 332 whether the time period for recording the threshold value has occurred. In this embodiment, the processor 112 is adapted to periodically record the threshold value in the memory 130 at a fixed frequency regardless of the change in the threshold value. The frequency with which the threshold value would be recorded in the memory 130 can vary dependent upon the implantation period of the cardiac device. For example, in one embodiment, the fixed frequency can be set to be relatively high, e.g., one a day during the acute period of implantation, and the processor 112 can be configured to reduce the set frequency to a lower value, e.g., once a week, during the chronic phase of implantation. Moreover, the data that is recorded in state 330 can be in any of a number of forms, such as actual magnitude and duration values, and corresponding times or even delta values and corresponding elapsed time period for compressed data storage in the memory 130.

As discussed above in reference to FIG. 4, the capture threshold value changes more significantly during the acute phase of implantation and then remains relatively constant during the chronic phase of implantation. Hence, the default frequency with which the measured threshold value is recorded in memory can be selected as to be higher during the acute phase of implantation than the chronic phase of implantation. Once the threshold values have been recorded in state 330, the processor 112 then continues pacing in the desired mode in state 334.

It will be appreciated from the foregoing description that the implantable cardiac device 100 is capable of periodically sensing a parameter, such as the capture threshold, at either a fixed frequency or a frequency that is selected based upon the change or volatility of the particular parameter. As the volatility of the particular parameter increases, the sampling rate of this particular parameter can also be increased and the frequency with which the measurement of the parameter can be recorded in the memory can also be increased. In this way, limited battery power can be conserved without a significant loss of important data. Further, the memory of the implantable cardiac device can be used to store data that is representative of periods of volatility of the parameter rather than the filled with measurements that are indicative of substantially no change in the particular parameter.

From the foregoing, it will be appreciated that the implantable cardiac device is capable of measuring various device or heart parameters and then recording the parameter measurements in the memory with greater frequency when the device parameter measurements are varying more significantly. However, when the device parameter measurements indicate that the device parameter is remaining stable, the processor is further adapted to limit the storing of values so as to conserve on memory space. In this way, data can be stored for subsequent review by a treating physician, but the system does not require the use of an extensive memory.

Although this embodiment of the present invention has shown, described and pointed out the fundamental novel features of the invention as applied to these embodiments, it will be understood that various omissions, substitutions, and changes in the form of the detail of the device illustrated may be made by those skilled in the art without departing from the spirit of the present invention. Consequently, the scope of the invention should not be limited to the foregoing description but should be defined by the appended claims.

What is claimed is:

1. An implantable cardiac stimulation device, comprising:

automatic testing means for automatically performing a periodic test relating to at least one of the patient's physiologic condition or the device's performance, and for producing a resultant output signal representative thereof; and processing means for adjusting the frequency at which the automatic testing means performs the periodic test based on a comparison of a current output signal to a previously output signal so that the automatic test is performed at a greater frequency when the output signal is volatile and at a lesser frequency when the output signal remains stable.

2. The device of claim 1, further comprising:

storage means for storing data representative of the output signal at a greater frequency when the output signal is volatile and at a lesser frequency when the output signal remains stable; and telemetry means for transferring the data stored in the storage means to an external programmer having a display screen capable of displaying the data as a function of time.

3. The device of claim 1, wherein the processing means comprises:

means for increasing the testing frequency when the difference between the current output signal and the previous output signal is greater than a preselected value.

4. The device of claim 1, wherein the processing means comprises:

means for decreasing the testing frequency when the difference between the magnitude of the output signal and the previous output signal is less than the preselected value.

5. A method of adjusting the frequency of automatic tests in an implantable cardiac device, the method comprising:

automatically performing a periodic test relating to at least one of the patient's physiologic condition or the device's performance;

producing a resultant output signal representative of the periodic test; and adjusting the frequency at which the periodic test is performed based on a comparison of a current output signal to a previously output signal so that the periodic test is performed at a greater frequency when the output signal is volatile and at a lesser frequency when the output signal remains stable.

6. The method of claim 5, further comprising the step of:

storing data representative of the output signal at a greater frequency when the output signal is volatile and at a lesser frequency when the output signal remains stable;

transferring the stored data to an external programmer having a display screen; and displaying the data as a function of time.

7. The device of claim 5, wherein the step of adjusting the frequency comprises the step of:

increasing the testing frequency when the difference between the current output signal and the previous output signal is greater than a preselected value.

8. The device of claim 7, wherein the step of adjusting the frequency comprises the step of:

decreasing the testing frequency when the difference between the current output signal and the previous output signal is less than a preselected value.

* * * * *